US011937968B2

(12) United States Patent
Engel (10) Patent No.: US 11,937,968 B2
(45) Date of Patent: Mar. 26, 2024

(54) POSITIONING A MEDICAL X-RAY IMAGING APPARATUS

(71) Applicant: KONINKLIJKE PHILIPS N.V., Eindhoven (NL)

(72) Inventor: Klaus Juergen Engel, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 372 days.

(21) Appl. No.: 17/298,577

(22) PCT Filed: Dec. 6, 2019

(86) PCT No.: PCT/EP2019/084043
§ 371 (c)(1),
(2) Date: May 30, 2021

(87) PCT Pub. No.: WO2020/115307
PCT Pub. Date: Jun. 11, 2020

(65) Prior Publication Data
US 2022/0022839 A1 Jan. 27, 2022

(30) Foreign Application Priority Data
Dec. 7, 2018 (EP) ..................................... 18211045

(51) Int. Cl.
*A61B 6/00* (2006.01)
*A61B 6/04* (2006.01)
(Continued)

(52) U.S. Cl.
CPC ............ *A61B 6/547* (2013.01); *A61B 6/0407* (2013.01); *A61B 6/08* (2013.01); *A61B 6/4476* (2013.01);
(Continued)

(58) Field of Classification Search
CPC ......... A61B 6/547; A61B 6/0407; A61B 6/08; A61B 6/4476; A61B 6/469; A61B 6/488;
(Continued)

(56) References Cited

U.S. PATENT DOCUMENTS 6,200,024 B1 3/2001 Negrelli
2002/0045817 A1 4/2002 Ichihashi
(Continued)

FOREIGN PATENT DOCUMENTS

CN 106999127 A 8/2017
JP H11347024 A 12/1999
WO 2006103580 A1 10/2006

OTHER PUBLICATIONS

International Search Report and Written Opinion of PCT/EP2019/084043, dated Jan. 21, 2020.
(Continued)

*Primary Examiner* — Courtney D Thomas (57) ABSTRACT

The present invention relates to medical X-ray imaging. In order to provide further facilitated positioning of a medical X-ray imaging apparatus, a device (10) for support in positioning a medical X-ray imaging apparatus is provided. The device comprises an input unit (12), a processing unit (14) and an output unit (16). The input unit is configured to receive a 3D motion-model of a currently used X-ray imaging apparatus; and to receive a 3D model of a subject suitable for a calculation of virtual X-ray projections. The input unit is also configured to receive current 3D spatial context data in relation to a current location and orientation of the X-ray imaging apparatus, the 3D spatial context data comprising at least one of the group of a current arrangement of an object support, a current position of the subject on the object support, and objects or persons currently located in a potential moving area of the X-ray imaging apparatus. The input unit is further configured to receive movement instruc-
(Continued)

tions for movement of the 3D motion-model. The processing unit is configured to adapt the 3D motion-model according to the movement instructions. The processing unit is also configured to generate a virtual X-ray projection of a region of interest based on the spatial arrangement of the 3D motion-model in relation to the 3D model of the subject. Further, the output unit is configured to provide image data of the virtual X-ray projection.

15 Claims, 3 Drawing Sheets

(51) Int. Cl.
  *A61B 6/08* (2006.01)
  *G06T 19/00* (2011.01)
  *G06V 20/64* (2022.01)
(52) U.S. Cl.
  CPC ............ *A61B 6/469* (2013.01); *G06T 19/00* (2013.01); *G06V 20/64* (2022.01); *G06T 2210/41* (2013.01)
(58) Field of Classification Search
  CPC ..... A61B 6/5294; A61B 6/5223; A61B 6/102; A61B 6/04; A61B 6/5247; A61B 6/548; A61B 6/032; G06T 19/00; G06T 2210/41; G06T 11/005; G06T 11/008; G06V 20/64

See application file for complete search history.

(56) References Cited

U.S. PATENT DOCUMENTS

| | | |
|---|---|---|
| 2005/0281374 A1 | 12/2005 | Cheng |
| 2014/0022353 A1 | 1/2014 | Hamersma |
| 2016/0104312 A1 | 4/2016 | Zino |
| 2017/0200317 A1 | 7/2017 | Hannemann |
| 2017/0322484 A1 | 11/2017 | Erhard |
| 2017/0347979 A1 | 12/2017 | Fehre |
| 2018/0043183 A1* | 2/2018 | Sheng .................. A61N 5/1047 |
| 2018/0228010 A1 | 8/2018 | Butani |

OTHER PUBLICATIONS

Mewes, A. et al "A Gesture-Controlled Projection Display for CT-Guided Interventions", Int. J. Cars, vol. 11, pp. 157-164, 2016.
Suhm, N. et al "Adapting the Fluoroscope to Image-Guided Surgery", Injury, Int. J. Car Injured, vol. 34, 2003, pp. 307-311.

* cited by examiner

POSITIONING A MEDICAL X-RAY IMAGING APPARATUS

CROSS-REFERENCE TO PRIOR APPLICATIONS

This application is the U.S. National Phase application under 35 U.S.C. § 371 of International Application No. PCT/EP2019/084043, filed on Dec. 6, 2019, which claims the benefit of European Patent Application No. 18211045.2, filed on Dec. 7, 2018. These applications are hereby incorporated by reference herein.

FIELD OF THE INVENTION

The present invention relates to positioning a medical X-ray imaging apparatus, and relates in particular to a device for support in positioning a medical X-ray imaging apparatus, to a medical X-ray imaging system and to a method for support in positioning a medical X-ray imaging apparatus.

BACKGROUND OF THE INVENTION

As an example, interventional C-arm systems provide X-ray images as projections through a patient in desired orientations. However, the desired orientation depends strongly on patient anatomy, procedure to be performed and orientation (or respective 2D-projection) of the region of interest. As an example, the interventional procedure might be a cardiac stent placement. The desired orientation for this procedure would be one where the region of interest (ROI) is ideally not covered by contrast-rich and/or strong attenuating bone structures, like the spine, and furthermore, the stent should be visible in a view perpendicular to the stent axis. An operator therefore makes a test image for checking if the orientation is best suited, and may switch to another orientation in a try-and-error manner. It has been shown that this approach is time consuming and may result in additional, even if only marginal, X-ray dose to patient and staff. As an example, WO 2006/103580 A1 relates to the observation of a catheter in a vessel system and describes support for finding an optimal projection direction. However, a plurality of X-ray projections is provided that are used for the determination of the optimal viewing angle.

SUMMARY OF THE INVENTION

There may thus be a need to provide further facilitated support in positioning of a medical X-ray imaging apparatus.

The object of the present invention is solved by the subject-matter of the independent claims; further embodiments are incorporated in the dependent claims. It should be noted that the following described aspects of the invention apply also for the device for support in positioning a medical X-ray imaging apparatus, for the medical X-ray imaging system and for the method for support in positioning a medical X-ray imaging apparatus.

According to the present invention, a device for support in positioning a medical X-ray imaging apparatus is provided. The device comprises an input unit, a processing unit and an output unit. The input unit is configured to receive a 3D motion-model of a currently used X-ray imaging apparatus. The input unit is also configured to receive a 3D model of a subject suitable for a calculation of virtual X-ray projections. The input unit is still further configured to receive movement instructions for movement of the 3D motion-model, whereby the movement instructions relate to a movement of the imaging apparatus to a target location for imaging or to a movement trajectory of the imaging apparatus along which imaging is intended to take place.

The processing unit is configured to adapt the 3D motion-model according to the movement instructions. The processing unit is further configured to generate a virtual X-ray projection of a region of interest based on the spatial arrangement of the 3D motion-model in relation to the 3D model of the subject. Further, the output unit is configured to provide image data of the virtual X-ray projection.

This provides the effect that a user is provided with a simulated situation with detailed information to determine a viewing angle to be applied for X-ray imaging without the further need for X-ray test runs. Besides the facilitated and intuitive workflow, this also means less X-ray dose to the subject and staff.

In an example, a C-arm imaging device can be virtually moved to specific viewing angles so as to generate a virtual exposure of a region of interest of a subject from said angle. Such virtual exposure may be checked by a physician, radiologist or other hospital staff member and, if the virtual image is deemed to be suitable for a following procedure, an actual movement of the real imaging device to a corresponding viewing angle (e.g. C-arm rotation and angulation) may be effectuated.

According to an example, the input unit is further configured to receive current 3D spatial context data in relation to a current location and orientation of the X-ray imaging apparatus, the 3D spatial context data comprising at least one of the group of a current arrangement of an object support, a current position of the subject on the object support, and objects or persons currently located in a potential moving area of the X-ray imaging apparatus. In certain examples, the processing unit is then configured to generate a current 3D scenery model based on the 3D motion-model, the 3D spatial context data and the 3D model of the subject. The processing unit is also configured to adapt the 3D scenery according to the adapted 3D motion-model. Further, the output unit may be configured to provide output data of the 3D scenery model.

According to an example, the processing unit is configured to continuously update the image data of the 3D scenery model and the image data of the virtual projection.

According to the present invention, also a medical X-ray imaging system is provided. The system comprises a movable X-ray imaging apparatus comprising an X-ray source and an X-ray detector, and an object support for receiving a subject. Further, a device for positioning a medical X-ray imaging apparatus according to one of the preceding examples is provided. The 3D motion-model corresponds to the movable X-ray imaging apparatus. The movable X-ray imaging apparatus and/or the object support comprise a motorized drive for positioning the X-ray source and X-ray detector and the object support in relation to each other based on the movement instructions for the movement of the 3D motion-model.

According to an example, the X-ray imaging apparatus comprises a C-arm structure carrying the X-ray source and the X-ray detector.

According to an example, the X-ray imaging system further comprises a spatial environment detection arrangement configured to detect a current 3D situation in relation to a current location and orientation of the X-ray imaging apparatus. The current 3D situation comprises at least one of the group of a current arrangement of the object support, a current position of the subject on the object support, and objects or persons currently located in a potential moving area of the X-ray imaging apparatus. The detected 3D situation is converted into the 3D spatial context data.

According to an example, the spatial environment detection arrangement comprises at least one of the group of one or more depth sensitive cameras and a combination of several cameras combined with 3D object recognition software.

According to the present invention, also a method for support in positioning a medical X-ray imaging apparatus is provided. The method comprises the following steps:
a1) receiving: a 3D motion-model of a currently used X-ray imaging apparatus and a 3D model of a subject suitable for a calculation of virtual X-ray projections
b) receiving movement instructions for movement of the 3D motion-model, the movement instructions relating to a movement of the imaging apparatus to a target location for imaging or to a movement trajectory of the imaging apparatus along which imaging is intended to take place;
c1) adapting the 3D motion-model according to the movement instructions;
d) generating a virtual X-ray projection of a region of interest based on the spatial arrangement of the 3D motion-model in relation to the 3D model of the subject; and
e1) providing image data of the virtual X-ray projection.

According to an aspect, virtual X-ray imaging is provided based on a one-to-one virtual model of a real C-arm system. This allows to find the most desired orientations for interventional X-ray imaging, e.g. of non-standard patient cases. As an intervention planning support, the operator can use the virtual model together with a patient model to search for the best matching C-arm orientation. The virtual X-ray imaging, i.e. X-ray images created by a computer model of a patient, is provided to help the doctor finding a most desired orientation for X-ray imaging before the actual intervention takes place. It thus serves as an intervention planning support. Optionally, during the following procedure, the C-arm is automatically moved, i.e. without detailed movement control by the user, into the most desired, i.e. final position.

According to an optional aspect, a real C-arm system and its corresponding virtual model are providing a scaled copy of the real system. A patient model includes the region of interest (ROI), e.g. re-used from preceding diagnostics or in adequate cases acquired for purpose of virtual X-ray imaging from typical volume-imaging systems, like e.g. magnet resonance tomography, computed tomography, or C-arm volume imaging. A virtual model of said C-arm system and said patient model simulates the X-ray projection for particular positions, orientations, and other (X-ray) image settings, and thus provides a simulated, but still sufficiently realistic X-ray image for particular settings defined by the operator.

Hence, a workflow is provided to support an operator in finding a most desired orientation using the virtual model. As an option, the most desired position can be stored and transferred to a C-arm system intended for usage. During the following procedure, the C-arm is moved into the desired position, rotation and/or angulation.

The provision of a virtual X-ray image is suitable for all interventional X-ray system with a movable X-ray imaging arrangement, e.g. for C-arm systems.

According to another aspect, the movement and positioning of an interventional C-arm system is provided by gestures or vocal commands, e.g. to support the approach for improvement of sterility in an operational room, and also to enhance user experience. To improve system and patient safety, the movement is at first performed in a virtual reality model. In virtual space, movement can be controlled by the user by multiple views on the scenery, e.g. displayed on a main monitor in an operational room in a hospital. Once the desired or preferred position is achieved in the virtual reality, which can also be referred to as a simulation, the movement and positioning of the real system is performed, for example automatically according to the positions provided by the virtual model.

In an option, a live-3D-sampled model of the interventional room situation is provided for improved accuracy.

The present invention relates to movable interventional X-ray system, for example C-arm systems that can be moved to position X-ray focal spot and detector relative to a patient for getting a desired X-ray view. By providing a virtual model scenery, it is possible to provide a separate interface that is easy to clean and to transform into a sterile state. Thus, for sterility reasons, touched terminals on the X-ray system itself are not required and the need is avoided for cover by foils or the like. Furthermore, for a positive and improved user experience, the operator can concentrate on achieving the position for X-ray imaging which matches best with his/her intentions and needs, and "blind" moving of the C-arm to find a good position is avoided. Instead of the operator switching to a stop-and-go mode to fine-tune positioning for the final position, the user can freely move the C-arm in the virtual world first to find the desired position. The target location and orientation is then transferred to the real-world for a controlled motorized driving of the C-ram or another type of X-ray system to the imaging position or imaging trajectory.

In other words, following the adaptation of the 3D motion model in accordance with the movement instructions, a user may verify the virtual X-ray projection being generated. If the virtual projection meets his expectations for example with regard to the position and orientation of a C-arm with respect to a patient, an actual movement of a real C-arm for subsequent image acquisition may be effectuated preferably in an automated manner.

In certain examples, the 3D scenery model information may be used to calculate a trajectory for actual movement of the real C-arm so as to avoid collisions between the C-arm and objects or persons in the vicinity of the C-arm, which are represented in the 3D scenery model.

In an option, a virtually modelled C-arm with a subject is displayed on a screen while the operator intends to position the C-arm. In a first part, the operator controls the C-arm e.g. by gestures or by voice until he/she finds a final position. In a second part, the C-arm is automatically moved, i.e. without detailed movement control by the user, into the final position.

According to an optional aspect, a software modelling and displaying relevant objects in 3D space is provided, e.g. at least the C-arm, the table and the patient. In an option, the main screen or display in the interventional room displays one or more pre-defined views on the virtual modelled scenery according to the choice of the operator. Further, by recognizing gestures or voices from the operator, these can be translated to control movement and positioning of the virtual C-arm and/or virtual table with a (virtual) patient. For example, this is provided by microphones with speech recognition, and/or by depth sensitive cameras e.g. tracking the movement of finger tips or recognizing defined gestures formed by the operator's hand.

According to an optional aspect, a system is provided that detects, e.g. samples, a live, i.e. current, 3D-position setup in an interventional room, including at least a recognition of a C-arm and a patient table, i.e. their shape and their position to each other, optionally also objects or persons within the movement range of the C-arm system. This provides the relevant objects in 3D space. In an example, one or more depth sensitive cameras, or a combination of several cameras combined with 3D object recognition software is provided. Thus, a live 3D virtual modelling of all relevant objects and the patient is provided, e.g. at least a modelling of the C-arm and its relative position to the subject. Hence, a virtual C-arm and/or patient table is first positioned according to the input of an operator. Next, an automatic or at least steered movement of the real system is provided towards the target positions indicated in the above virtual system. Any objects or obstructions in the movement range of the C-arm can be adequately considered for the determination of the movement trajectory; in case that no suitable safe trajectory can be found, the operator can be warned about the safety problem.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Certain embodiments will now be described in greater details with reference to the accompanying drawings. In the following description, like drawing reference numerals are used for like elements, even in different drawings. The matters defined in the description, such as detailed construction and elements, are provided to assist in a comprehensive understanding of the exemplary embodiments. Also, well-known functions or constructions are not described in detail since they would obscure the embodiments with unnecessary detail. Moreover, expressions such as "at least one of", when preceding a list of elements, modify the entire list of elements and do not modify the individual elements of the list.

Figure 1:
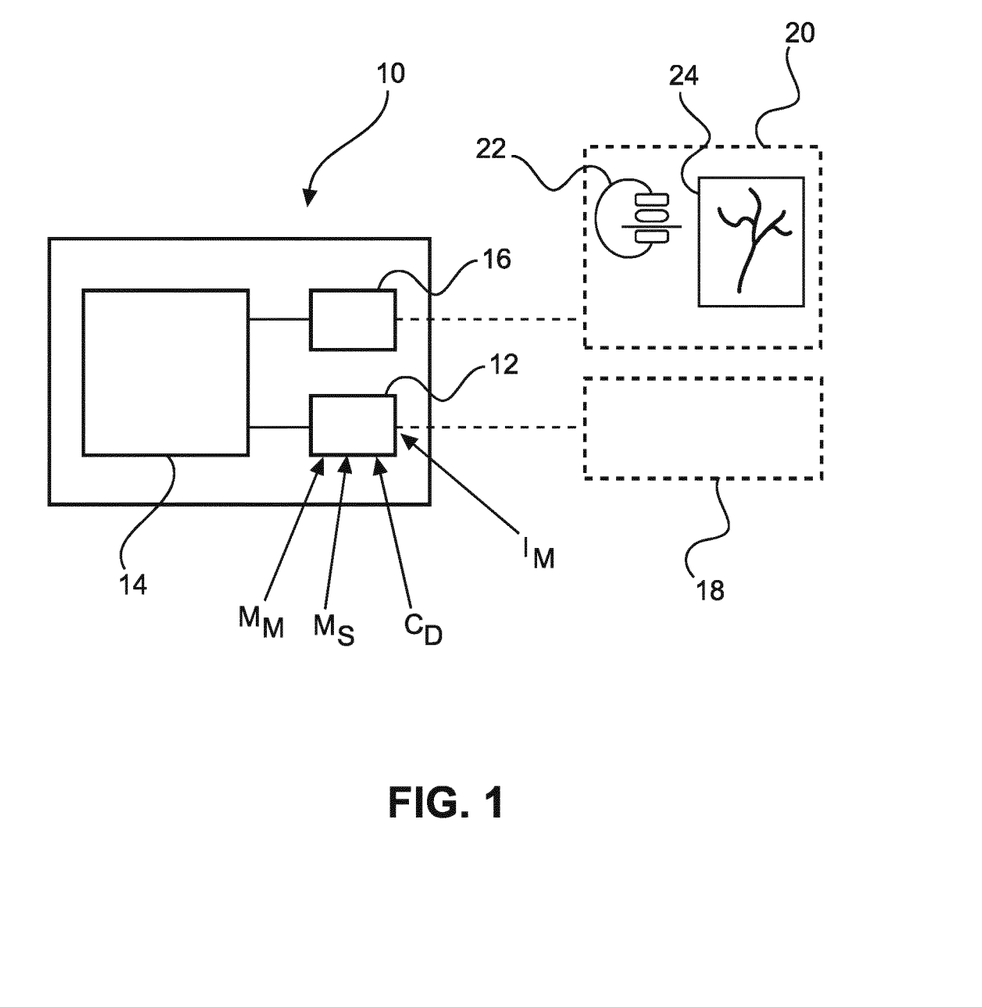
FIG. 1 schematically shows an example of a device for support in positioning a medical X-ray imaging apparatus.

FIG. 1 schematically shows a device 10 for support in positioning a medical X-ray imaging apparatus. The device 10 comprises an input unit 12, a processing unit 14 and an output unit 16. The input unit 12 is configured to receive a 3D motion-model $M_M$ of a currently used X-ray imaging apparatus; and to receive a 3D model $M_S$ of a subject suitable for a calculation of virtual X-ray projections.

In certain examples, the input unit 12 may also be configured to receive current 3D spatial context data $C_D$ in relation to a current location and orientation of the X-ray imaging apparatus. The 3D spatial context data comprises at least one of the group of a current arrangement of an object support, a current position of the subject on the object support, and objects or persons currently located in a potential moving area of the X-ray imaging apparatus.

The input unit 12 is further configured to receive movement instructions $I_M$ for movement of the 3D motion-model. These movement instructions relate to a movement of the imaging apparatus to a target location for imaging or to a movement trajectory of the imaging apparatus along which imaging is intended to take place.

The processing unit 14 is configured to adapt the 3D motion-model according to the movement instructions. The processing unit 14 is also configured to generate a virtual X-ray projection of a region of interest based on the spatial arrangement of the 3D motion-model in relation to the 3D model of the subject. Further, the output unit 16 is configured to provide output data of the virtual X-ray projection.

In an example, the X-ray imaging apparatus is a C-arm X-ray imaging system where source and detector are mounted to opposing ends of a common C-arm.

In another example, the X-ray imaging apparatus comprises individual movable supports for source and detector.

The 3D model of the subject may be based on pre-acquired image data of the subject.

In an example, the 3D model of the subject is based on a standard 3D model which is adapted to the current subject. In a further example, a plurality of different types of standard 3D models is provided and a type is chosen that shows most similarity with the current subject.

In another example, the 3D model of the subject is based on pre-acquired image data of the current subject, such as magnet resonance tomography (MRT), X-ray computed tomography (CT), or X-ray C-arm volume imaging.

The term "persons" in "objects or persons" comprises e.g. medical staff such as the surgeon and assisting persons. The term "objects" in "objects or persons" comprises e.g. equipment used during the intervention.

The term "medical" relates to image acquisition in the context of medical aspects, for example imaging provided during an interventional procedure, or imaging for examination of a subject and the like.

The object support can also be referred to as a patient table.

The term "subject" may also be referred to as individual. The "subject" may further also be referred to as patient, although it is noted that this term does not indicate whether any illness or disease is actually present with the subject.

The term "suitable for a calculation of virtual X-ray projections" relates to 3D data which has respective information that is needed to simulate an X-ray image. Besides a sufficient resolution, also the structural information should be available in view of simulating attenuation of radiation.

The current location and orientation can also be referred to as spatial arrangement.

In an option, not further shown in detail, the processing unit 14 is configured to generate a current 3D scenery model based on the 3D motion-model, the 3D spatial context data and the 3D model of the subject. The processing unit 14 is also configured to adapt the 3D scenery according to the adapted 3D motion-model. Further, the output unit 16 is configured to provide image data of the 3D scenery model.

In another option, not further shown in detail, the processing unit 14 is configured to limit the adaptation of the 3D motion-model based on motion-constraints given by the current 3D spatial context data.

In another option, not further shown in detail, the processing unit 14 is configured to adapt the 3D model of the subject to the current spatial arrangement of the subject on the object support.

In an example, the X-ray imaging apparatus comprises an X-ray source and an X-ray detector. For example, the X-ray source and the X-ray detector are arranged on a common movable support like a C-arm structure. In a further example, the X-ray source and the X-ray detector are each mounted to individual movable support structures like robot arms.

In another option, not further shown in detail, the processing unit 14 is configured to continuously update the image data of the 3D scenery model and the image data of the virtual projection.

In an option, only the image data of the 3D scenery model is continuously updated. In another option, only the image data of the virtual projection is continuously updated. In a further option, the image data of the 3D scenery model and the image data of the virtual projection are continuously updated.

In an example, the term "continuously" relates to a real-time reception of the user. For example, a delay of maximum 1 second is provided, e.g. maximum 0.5 second.

In an example, 5 updated images per second are provided. In a further example, a higher frame-rate of updated images is provided. As an example, a frame-rate of approximately 20 to 30 images per second, e.g. 24 frames per second, provide an impression of a fluent flow of images.

In an example, a continuous sequence of virtual X-ray projections is provided to the user for the duration when the 3D motion-model is adapted based on the movement instructions.

In another example, a continuous sequence of virtual X-ray projections is provided to the user for the duration of movement and also for periods of no change of motion of the 3D motion-model of the X-ray imaging apparatus.

In another option, not further shown in detail, the input unit comprises a user interface 18 for entering the movement instructions.

In an example, the user interface is a gesture control device configured to generate movement instructions based on predetermined user gestures. For example, the gestures are recognized via cameras. In a further example, interactive glove devices are provided. In a still further example, handheld devices are provided to be moved by the user.

In an example, the user interface is a voice control device configured to generate movement instructions based on predetermined user voice commands.

In another example, the user interface is a joystick control device configured to generate movement instructions based on user control movements.

In a further example, the user interface is provided as a manually movable scaled model of the used X-ray imaging apparatus. The user can grasp the model and perform the intended movement with the model of the X-ray imaging apparatus. The movement of the model is tracked and translated into respective movement instructions.

In another option, not further shown in detail, the output unit comprises a display 20. In an example, the display 20 is configured to display the 3D scenery model, e.g. from at least one perspective, optionally also from multiple perspectives (indicated with reference numeral 22 in a left part of the display) and also to display the virtual X-ray projection (indicated with reference numeral 24 in a right part of the display, schematically showing a virtual X-ray projection of a vascular structure of the object as if seen by the currently chosen imaging configuration).

It is noted that the display 20 may be provided as a separate display or monitor. However, also an anyway existing display can be used for the task of presenting the scenery model or presenting any other content or function.

In certain examples, image data of the 3D motion model, 3D scenery model and/or the virtual projection are presented to a user in an Augmented Reality (AR) environment.

Optionally, the AR environment also comprises the user interface for entering movement instructions. That is, for example, a user may manipulate the 3D motion model in the AR environment by means of gestures, and the adapted 3D motion model and corresponding virtual projection may then be presented to him. When the user verifies the virtual device location by means of a further gesture, the real system may be automatically moved to the corresponding location.

The generated 3D scenery model thus illustrates a possible arrangement of the real-world situation. The user can verify if the instructed movements result in a spatial orientation that the user had in mind. Further, by providing the virtual X-ray projection, the user can verify if a respective X-ray image would actually show the intended view.

In certain examples, upon such user verification, the 3D scenery model information may then be used to calculate a trajectory for actual movement of the real C-arm so as to avoid collisions between the C-arm and objects or persons in the vicinity of the C-arm, which are represented in the 3D scenery model. The actual movement may then be effectuated by means of a C-arm control unit, thus moving the C-arm along the calculated trajectory to the location, i.e. position, rotation and/or angulation, corresponding to the intended view.

Figure 2:
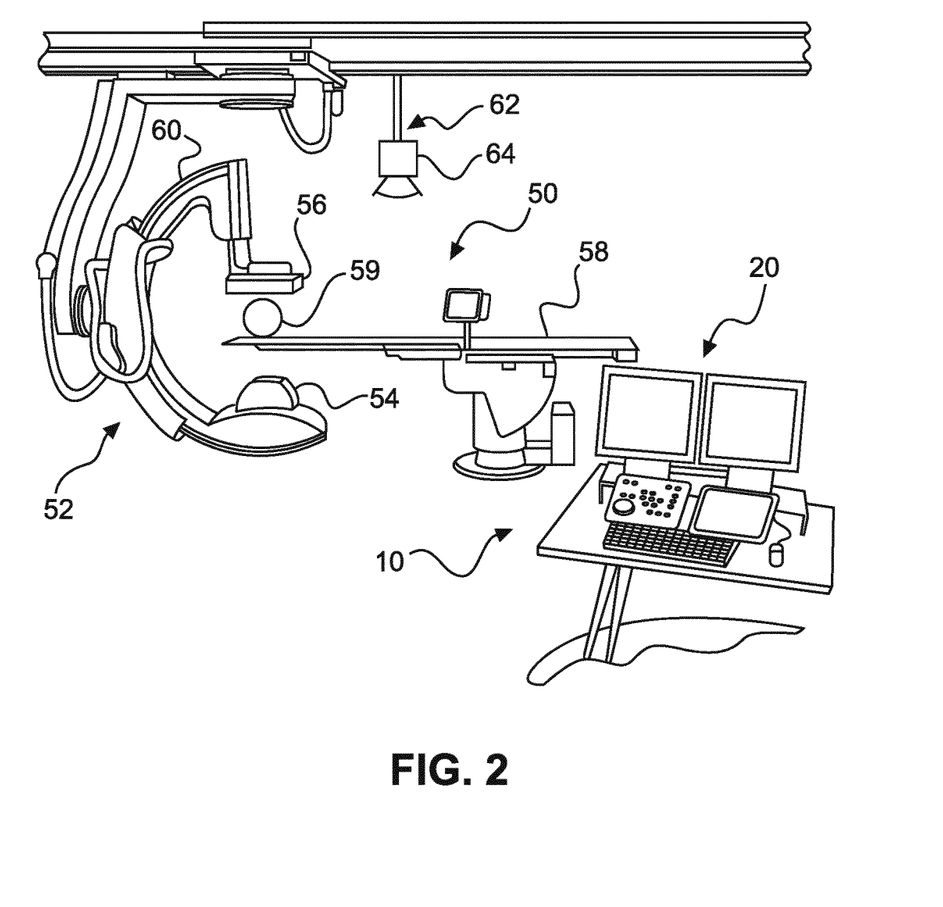
FIG. 2 schematically shows an example of a medical X-ray imaging system.

FIG. 2 schematically shows an example of a medical X-ray imaging system 50. The system 50 comprises a movable X-ray imaging apparatus 52 with an X-ray source 54 and an X-ray detector 56. The system 50 further comprises an object support 58 for receiving a subject 59. Still further, an example of the device 10 for positioning a medical X-ray imaging apparatus according to one of the preceding examples is provided. The 3D motion-model corresponds to the movable X-ray imaging apparatus. Further, the movable X-ray imaging apparatus and/or the object support comprise a motorized drive for positioning the X-ray source and X-ray detector and the object support in relation to each other based on the movement instructions for the movement of the 3D motion-model.

The motorized movement of the C-arm or other form of support for the source/detector in combination with a touchless operation or operation via remote control provides an easy to keep sterile imaging system.

In another option, not further shown in detail, the movable X-ray imaging apparatus 52 comprises a C-arm structure 60 carrying the X-ray source and the X-ray detector.

In another option, also not further shown in detail, the X-ray imaging system further comprises a spatial environment detection arrangement 62 configured to detect a current 3D situation in relation to a current location and orientation of the X-ray imaging apparatus, the current 3D situation comprising at least one of the group of a current arrangement of the object support, a current position of the subject on the object support, and objects or persons currently located in a potential moving area of the X-ray imaging apparatus. The detected 3D situation is converted into the 3D spatial context data. In another option, also not further shown in detail, the spatial environment detection arrangement comprises at least one of the group of one or more depth sensitive cameras 64 and a combination of several cameras combined with 3D object recognition software.

Figure 3:
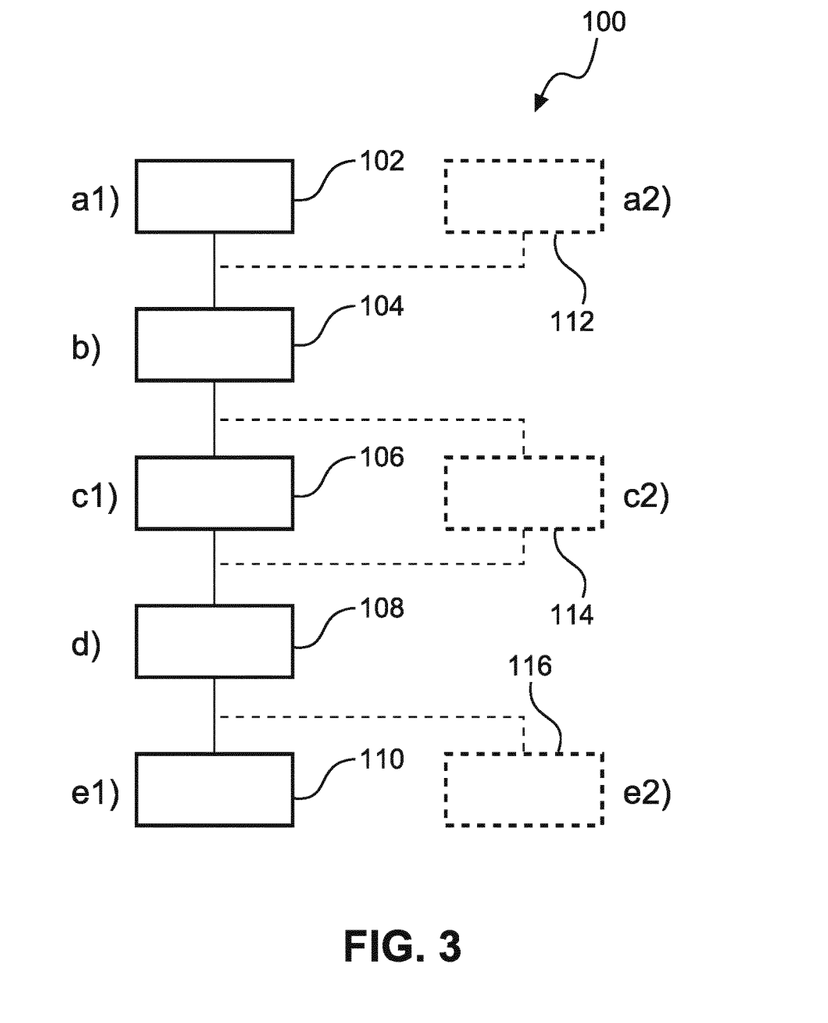
FIG. 3 shows steps of an example of a method for support in positioning a medical X-ray imaging apparatus.

FIG. 3 shows steps of an example of a method 100 for support in positioning a medical X-ray imaging apparatus. The method 100 comprises the following steps:

In a first step 102, also referred to as step a1), a 3D motion-model of a currently used X-ray imaging apparatus and a 3D model of a subject suitable for a calculation of virtual X-ray projections are received.

In a second step 104, also referred to as step b), movement instructions for movement of the 3D motion-model are received. The movement instructions relate to a movement of the imaging apparatus to a target location for imaging or to a movement trajectory of the imaging apparatus along which imaging is intended to take place; In a third step 106, also referred to as step c1), the 3D motion-model is adapted according to the movement instructions.

In a fourth step 108, also referred to as step d), a virtual X-ray projection of a region of interest is generated based on the spatial arrangement of the 3D motion-model in relation to the 3D model of the subject.

In a fifth step 110, also referred as step e1), image data of the virtual X-ray projection is provided.

In an option, indicated with hashed lines in FIG. 3, it is further provided:

a2) receiving current 3D spatial context data in relation to a current location and orientation of the X-ray imaging apparatus; the 3D spatial context data comprising at least one of the group of a current arrangement of an object support, a current position of the subject on the object support, and objects or persons currently located in a potential moving area of the X-ray imaging apparatus and generating 112 a current 3D scenery model based on the 3D motion-model, the 3D spatial context data and the 3D model of the subject;

c2) adapting 114 the 3D scenery according to the adapted 3D motion-model; and e2) providing 116 image data of the 3D scenery model.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit or be distributed over more than one computer units, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

Aspects of the invention may be implemented in a computer program product, which may be a collection of computer program instructions stored on a computer readable storage device which may be executed by a computer. The instructions of the present invention may be in any interpretable or executable code mechanism, including but not limited to scripts, interpretable programs, dynamic link libraries (DLLs) or Java classes. The instructions can be provided as complete executable programs, partial executable programs, as modifications to existing programs (e.g. updates) or extensions for existing programs (e.g. plugins). Moreover, parts of the processing of the present invention may be distributed over multiple computers or processors.

As discussed above, the processing unit, for instance a controller implements the control method. The controller can be implemented in numerous ways, with software and/or hardware, to perform the various functions required. A processor is one example of a controller which employs one or more microprocessors that may be programmed using software (e.g. microcode) to perform the required functions. A controller may however be implemented with or without employing a processor, and also may be implemented as a combination of dedicated hardware to perform some functions and a processor (e.g. one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

This exemplary embodiment of the invention covers both, a computer program that right from the beginning uses the invention and a computer program that by means of an update turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section. A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated, and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A device for support in positioning a medical X-ray imaging apparatus, comprising:
   an input unit;
   a processing unit; and
   an output unit;
   wherein the input unit is configured i) to receive a 3D motion-model of a currently used X-ray imaging apparatus; and ii) to receive a 3D model of a subject suitable for a calculation of virtual X-ray projections; and iii) to receive movement instructions for movement of the 3D motion-model, the movement instructions relating to a movement of the currently used X-ray imaging apparatus to a target location for imaging or to a movement trajectory of the currently used X-ray imaging apparatus along which imaging is intended to take place;
   wherein the processing unit is configured to adapt the 3D motion-model according to the movement instructions; and to generate a virtual X-ray projection of a region of interest based on a spatial arrangement of the adapted 3D motion-model in relation to the 3D model of the subject; and
   wherein the output unit is configured to provide image data of the virtual X-ray projection.

2. The device of claim 1, wherein the input unit is further configured to receive current 3D spatial context data in relation to a current location and orientation of the currently used X-ray imaging apparatus, the current 3D spatial context data comprising at least one of a current arrangement of an object support, a current position of the subject on the object support, and objects or persons currently located in a potential moving area of the currently used X-ray imaging apparatus.

3. The device according to claim 2, wherein the processing unit is configured to generate a current 3D scenery model based on the 3D motion-model, the current 3D spatial context data and the 3D model of the subject; and to adapt the 3D scenery according to the adapted 3D motion-model; and
   wherein the output unit is configured to provide image data of the 3D scenery model.

4. The device according to claim 2, wherein the processing unit is configured to limit the adaptation of the 3D motion-model based on motion-constraints given by the current 3D spatial context data.

5. The device according to claim 2, wherein the processing unit is configured to adapt the 3D model of the subject to a current spatial arrangement of the subject on the object support.

6. The device according to claim 3, wherein the processing unit is configured to continuously update the image data of the 3D scenery model and the image data of the virtual projection.

7. The device according to claim 1 wherein the input unit comprises a user interface for entering the movement instructions.

8. A medical X-ray imaging system, comprising:
   a movable X-ray imaging apparatus comprising an X-ray source and an X-ray detector;
   an object support for receiving a subject;
   a device for positioning the movable X-ray imaging apparatus according to claim 1;
   wherein the 3D motion-model corresponds to the movable X-ray imaging apparatus; and
   wherein at least one of the movable X-ray imaging apparatus or the object support comprise a motorized drive for positioning the X-ray source and X-ray detector and the object support in relation to each other based on the movement instructions for the movement of the 3D motion-model.

9. The X-ray imaging system according to claim 8, wherein the movable X-ray imaging apparatus comprises a C-arm structure carrying the X-ray source and the X-ray detector.

10. The X-ray imaging system according to claim 8, further comprising a spatial environment detection arrangement configured to detect a current 3D situation in relation to a current location and orientation of the movable X-ray imaging apparatus, the current 3D situation comprising at least one of of a current arrangement of the object support, a current position of the subject on the object support, and objects or persons currently located in a potential moving area of the movable X-ray imaging apparatus; and wherein the detected 3D situation is converted into 3D spatial context data.

11. The X-ray imaging system according to claim 10, wherein the spatial environment detection arrangement comprises at least one of one or more depth sensitive cameras and a combination of several cameras combined with 3D object recognition software.

12. A method for support in positioning a medical X-ray imaging apparatus, comprising:
   receiving a 3D motion-model of a currently used X-ray imaging apparatus and a 3D model of a subject suitable for a calculation of virtual X-ray projections;
   receiving movement instructions for movement of the 3D motion-model, the movement instructions relating to a movement of the currently used X-ray imaging apparatus to a target location for imaging or to a movement trajectory of the currently used X-ray imaging apparatus along which imaging is intended to take place;
   adapting the 3D motion-model according to the movement instructions;
   generating a virtual X-ray projection of a region of interest based on a spatial arrangement of the 3D motion-model in relation to the 3D model of the subject; and
   providing image data of the virtual X-ray projection.

13. The method according to claim 12, further comprising:
   receiving current 3D spatial context data in relation to a current location and orientation of the currently used X-ray imaging apparatus, the current 3D spatial context data comprising at least one of a current arrangement of an object support, a current position of the subject on the object support, and objects or persons currently located in a potential moving area of the currently used X-ray imaging apparatus;
   generating a current 3D scenery model based on the 3D motion-model, the current 3D spatial context data and the 3D model of the subject;
   adapting the 3D scenery according to the adapted 3D motion-model; and
   providing image data of the 3D scenery model.

14. A computer program for controlling an apparatus, which, when being executed by a processing unit, is adapted to perform the method of claim 12.

15. A non-transitory computer readable medium having stored the program of claim 14.

* * * * *